United States Patent [19]

Camenzind et al.

[11] Patent Number: 5,300,243
[45] Date of Patent: Apr. 5, 1994

[54] LUBRICANT COMPOSITION

[75] Inventors: Hugo Camenzind, Fribourg; Peter Nesvadba, Marly, both of Switzerland

[73] Assignee: Ciba-Geigy Corporation, Ardsley, N.Y.

[21] Appl. No.: 24,926

[22] Filed: Feb. 26, 1993

Related U.S. Application Data

[60] Continuation of Ser. No. 781,790, Oct. 23, 1991, abandoned, which is a division of Ser. No. 454,323, Dec. 21, 1989, Pat. No. 5,084,195.

[30] Foreign Application Priority Data

Dec. 28, 1988 [CH] Switzerland ............ 4828/88

[51] Int. Cl.$^5$ ............... C10M 135/14; C10M 135/16
[52] U.S. Cl. ........................... 252/47.5; 252/78.1
[58] Field of Search ..................... 252/47.5, 78.1

[56] References Cited

U.S. PATENT DOCUMENTS

| | | | |
|---|---|---|---|
| 2,316,903 | 4/1943 | Van Ess et al. | 252/47.5 |
| 2,599,737 | 6/1952 | Adelson | 252/47.5 |
| 4,225,450 | 9/1980 | Rosenberger | 252/47.5 |
| 4,659,853 | 4/1987 | Fu et al. | 558/19 |
| 5,084,195 | 1/1992 | Camenzind et al. | 252/47.5 |

FOREIGN PATENT DOCUMENTS 1443886  5/1972  Fed. Rep. of Germany .

OTHER PUBLICATIONS

Derwent Abst. 72-36105T/23 (1972).
K. H. König et al., Chem. Ber. 120, 1251 (1987).
L. L. Whitfield et al., Synthesis, 1985, 423.
J. C. Brindley et al, J. Chem. Soc. Perkin Trans. I, 1987, 1153.
H. Hartmann et al., J. Prakt Chem. 315, 144 (1973).
E. Schröpl et al., Pharmaz Zhalle 107,493 (1968).
Chemical Abst. 78, 43396m (1973).

*Primary Examiner*—Jerry D. Johnson
*Attorney, Agent, or Firm*—Luther A. R. Hall

[57] ABSTRACT

A composition comprising
a) a lubricant or a hydraulic fluid and
b) at least one compound of the general formula I

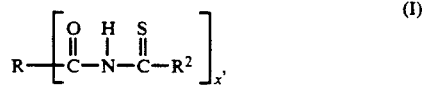

in which x=1 or 2 and,
if x=1,
R is as defined for $R^1$ or $R^3$—O— or,
if x=2,
R is as defined for $R^8$, and
$R^1$ and $R^3$ are, for example, alkyl, cycloalkyl, alkenyl, phenyl, naphthyl, aralkyl or alkaryl, or alkyl, cycloalkyl, alkenyl, phenyl, naphthyl, aralkyl or alkaryl, which are monosubstituted or polysubstituted by groups from the series comprising halogen, cyano, nitro, e.g. —OCH$_3$ or e.g. —COOCH$_3$, or alkyl, cycloalkyl, alkenyl, aralkyl or alkaryl which are interrupted by one or more groups from the series comprising —O—, —S—, —NH—,

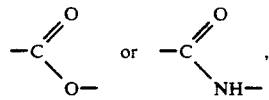

or alkyl, cycloalkyl, alkenyl, aralkyl or alkaryl which are monosubstituted or polysubstituted by groups from the series comprising halogen, cyano, nitro, e.g. —OCH$_3$ or e.g. —COOCH$_3$ and interrupted by one or more groups from the series comprising —O—, —S—, —NH—,

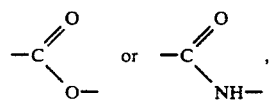

and
$R^2$ is $NR^4R^5$, —OR$^6$ or —SR$^7$, and (Abstract continued on next page.)

$R^4$ and $R^5$ are identical or different and are, for example,

—H, alkyl, phenyl, naphthyl, aralkyl or alkaryl, or $R^4$ and $R^5$, together with the N atom linking them, form, for example, a piperidine or morpholine radical, and $R^6$ and $R^7$ can be alkyl which may be interrupted by one or more groups from the series comprising —O—, —S—, —NH—,

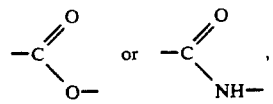

or are, for example, phenyl, naphthyl, alkaryl or aralkyl, and $R^8$ can be alkylene which may be interrupted by at least one —O— group or alkylidene which may be interrupted by at least one —O— group. Some of the compounds of the formula I are novel. The compositions show an improved stability towards oxidative degradation, confer protection under extreme pressures and reduce frictional wear.

11 Claims, No Drawings

LUBRICANT COMPOSITION

This is a continuation of application Ser. No. 07/781,790, filed on Oct. 23, 1991, now abandoned, which is a divisional of application Ser. No. 07/454,323, filed on Dec. 21, 1989, now U.S. Pat. No. 5,084,195, issued on Jan. 28, 1992.

The present invention relates to novel compositions comprising a lubricant or a hydraulic fluid, and at least one compound which acts as wear protection for metal components subject to frictional wear and as an antioxidant in lubricants. The present invention also relates to novel compounds and to the use of the compositions and novel compounds.

It is known to provide lubricants, for example lubricating oils on a mineral and/or synthetic basis, with additives which act, for example, as wear protection for metal components and are thus capable of reducing the wear on metal components subject to frictional wear. It is also known to add antioxidants to the lubricants, in order to improve the stability and activity or to preserve these over prolonged periods.

It is also known, for example from WO 87/02,358, that phosphorus-containing compounds cannot be used without reservations as lubricating oil additives in lubricating oils for internal combustion engines which are fitted with a catalytic exhaust gas purification system. It is suspected that phosphorus-containing compounds deactivate the catalyst (cf. H. S. Gandhi et al., Applied Catalysis 3, (1982), 79-88).

In WO 87/02,358, thiadiazoles and salts thereof are described as lubricant additives which do not contain any phosphorus and with which, therefore, the adverse aspects described do not arise.

U.S. Pat. No. 4,659,853 has disclosed derivatives of isothiocyanates, without their use being explained in greater detail.

With a view to reduced combustion chamber deposits, more stringent demands are nowadays also made with respect to a low ash content of the lubricant additives.

It is the object of the present invention to provide lubricant compositions which contain additives which protect the metal components from extreme pressures and frictional wear, i.e. which represent a wear protection, and which protect the lubricant from oxidative degradation, without the lubricant additive exerting, for example, harmful effects on a catalytic exhaust gas purification system.

According to the invention, this is achieved by a composition comprising
a) a lubricant or a hydraulic fluid and
b) at least one compound of the general formula I

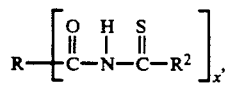   (I)

in which x=1 or 2 and,
if x=1,
R is as defined for $R^1$ or $R^3$—O— or,
if x=2,
R is as defined for $R^8$, and
$R^1$ and $R^3$ are alkyl having 1 to 25 C atoms, an unsubstituted or $C_1$-$C_8$alkyl-substituted cycloalkyl group having 5 to 12 ring C atoms, an unsubstituted or $C_1$-$C_8$alkyl-substituted $C_5$-$C_{12}$cycloalkyl-$C_1$-$C_4$alkyl group, alkenyl having 2 to 18 C atoms, phenyl, naphthyl, $C_7$-$C_{18}$aralkyl or $C_7$-$C_{18}$alkaryl, or $R^1$ and $R^3$ are alkyl having 1 to 25 C atoms, an unsubstituted or $C_1$-$C_8$alkyl-substituted cycloalkyl group having 5 to 12 ring C atoms, an unsubstituted or $C_1$-$C_8$alkyl-substituted $C_5$-$C_{12}$cycloalkyl-$C_1$-$C_4$alkyl group, alkenyl having 2 to 18 C atoms, phenyl, naphthyl, $C_7$-$C_{18}$aralkyl or $C_7$-$C_{18}$alkaryl, each of which are monosubstituted or polysubstituted by groups from the series comprising halogen, cyano, nitro, —$OR^a$ or —$COOR^b$, or $R^1$ and $R^3$ are alkyl having 2 to 25 C atoms, an unsubstituted or $C_1$-$C_8$alkyl-substituted cycloalkyl group having 3 to 10 ring C atoms, an unsubstituted or $C_1$-$C_8$alkyl-substituted $C_3$-$C_{12}$cycloalkyl-$C_1$-$C_4$alkyl group, alkenyl having 3 to 18 C atoms, $C_7$-$C_{18}$aralkyl or $C_7$-$C_{18}$alkaryl, each of which are interrupted by one or more groups from the series comprising —O—, —S—, —NH—,

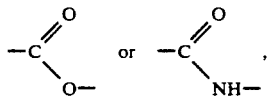

$C_7$-$C_{18}$aralkyl or $C_7$-$C_{18}$alkaryl being interrupted only in the alkyl radicals, or $R^1$ and $R^3$ are alkyl having 2 to 25 C atoms, an unsubstituted or $C_1$-$C_8$alkyl-substituted cycloalkyl group having 3 to 10 ring C atoms, an unsubstituted or $C_1$-$C_8$alkyl-substituted $C_3$-$C_{12}$cycloalkyl-$C_1$-$C_4$alkyl group, alkenyl having 3 to 18 C atoms, $C_7$-$C_{18}$aralkyl or $C_7$-$C_{18}$alkaryl, each of which are monosubstituted or polysubstituted by groups from the series comprising halogen, cyano, nitro, —$OR^a$ or —$COOR^b$ and are each interrupted by one or more groups from the series comprising —O—, —S—, —NH—,

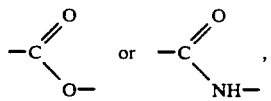

$C_7$-$C_{18}$aralkyl or $C_7$-$C_{18}$alkaryl being interrupted only in the alkyl radicals, $R^a$ being as defined for $R^3$ with the exception of —$OR^a$ and $R^b$ being as defined for $R^6$, and $R^2$ is —$NR^4R^5$, —$OR^6$ or —$SR^7$, and $R^4$ and $R^5$ are identical or different and are —H, alkyl having 1 to 23 C atoms, an unsubstituted or $C_1$-$C_8$alkyl-substituted cycloalkyl group having 5 to 12 ring C atoms, an unsubstituted or $C_1$-$C_8$alkyl-substituted $C_5$-$C_{12}$cycloalkyl-$C_1$-$C_4$alkyl group, phenyl, naphthyl, $C_7$-$C_{18}$aralkyl or $C_7$-$C_{18}$alkaryl, or $R^4$ and $R^5$, together with the N atom linking them, form a piperidine, morpholine, hexamethylenimine (perhydroazepine), pyrrolidine, piperazine or 1-methylpiperazine radical, and $R^6$ and $R^7$ are alkyl having 1 to 18 C atoms or alkyl having 2 to 20 C atoms which is interrupted by one or more groups from the series comprising —O—, —S—, —NH—,

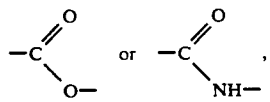

or an unsubstituted or $C_1$-$C_8$alkyl-substituted cycloalkyl group having 5 to 12 ring C atoms, an unsubstituted or $C_1$-$C_8$alkyl-substituted $C_5$-$C_{12}$cycloalkyl-$C_1$-$C_4$alkyl group, an unsubstituted or $C_1$-$C_8$alkyl-substituted $C_3$-$C_{12}$cycloalkyl-$C_1$-$C_4$alkyl group which is interrupted by one or more groups from the series comprising —O—, —S—, —NH—,

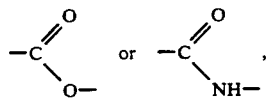

or phenyl, naphthyl, $C_7$-$C_{18}$alkaryl or $C_7$-$C_{18}$aralkyl, and $R^8$ is alkylene having 1 to 18 C atoms, alkylene having 2 to 18 C atoms and interrupted by at least one —O— group, alkylidene having 2 to 20 C atoms or alkylidene having 3 to 20 C atoms and interrupted by at least one —O— group.

$R^1$ and $R^3$ can, for example, be alkyl having 1 to 25 C atoms, an unsubstituted or $C_1$-$C_8$alkyl-substituted cycloalkyl group having 5 to 12 ring C atoms, alkenyl having 2 to 18 C atoms, phenyl, naphthyl, $C_7$-$C_{18}$aralkyl or $C_7$-$C_{18}$alkaryl, each of which are mono-, di- or tri-substituted, preferably monosubstituted, by a group from the series comprising halogen, cyano, nitro, —OR$^a$ or —COOR$^b$, or $R^1$ and $R^3$ can, for example, be alkyl having 2 to 25 C atoms, an unsubstituted or $C_1$-$C_8$alkyl-substituted cycloalkyl group having 5 to 12 ring C atoms, alkenyl having 3 to 18 C atoms, $C_8$-$C_{18}$aralkyl or $C_8$-$C_{18}$alkaryl, each of which are interrupted by one, two or three, preferably one, group from the series comprising —O—, —S—, —NH—,

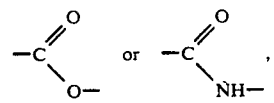

$C_8$-$C_{18}$aralkyl or $C_8$-$C_{18}$alkaryl being interrupted only in the alkyl radicals, or $R^1$ and $R^3$ can, for example, be alkyl having 2 to 25 C atoms, an unsubstituted or $C_1$-$C_8$alkyl-substituted cycloalkyl group having 5 to 12 ring C atoms, alkenyl having 3 to 18 C atoms, $C_8$-$C_{18}$aralkyl or $C_8$-$C_{18}$alkaryl, each of which are mono-, di- or tri-substituted, preferably monosubstituted, by a group from the series comprising halogen, cyano, nitro, —OR$^a$ or —COOR$^b$ and are each interrupted by one, two or three, preferably one, group from the series comprising —O—, —S—, —NH—,

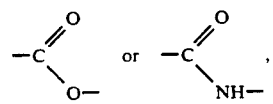

$C_8$-$C_{18}$aralkyl or $C_8$-$C_{18}$alkaryl being interrupted only in the alkyl radicals, with $R^a$ and $R^b$ being as defined, and $R^6$ and $R^7$ can, for example, be alkyl having 2 to 20 C atoms and interrupted by one, two or three, preferably one, group from the series comprising —O—, —S—, —NH—,

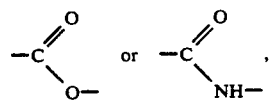

$R^8$ can, for example, be alkylene having 1 to 18 C atoms and interrupted by one —O— group, or alkylidene having 3 to 20 C atoms and interrupted by one —O— group.

Advantageous compositions contain at least one compound of the general formula I, in which $R^1$ and $R^3$ are alkyl having 1 to 18 C atoms, cycloalkyl having 5 to 8 ring C atoms, phenyl or $C_7$-$C_{18}$aralkyl, $R^4$ and $R^5$ are identical or different and are —H, alkyl having 1 to 18 C atoms, cycloalkyl having 5–12 ring C atoms or phenyl, and $R^6$ and $R^7$ are alkyl having 1 to 18 C atoms, a cycloalkyl group having 5 to 8 ring C atoms or alkyl having 2 to 20 C atoms and interrupted by one group

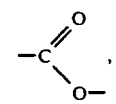

or phenyl or $C_7$-$C_{18}$aralkyl, and $R^8$ is alkylene having 1 to 18 C atoms or alkylidene having 2 to 20 C atoms.

In an alkyl radical $R^1$ or $R^3$ having 1 to 25 C atoms, the alkyl group can be straight-chain or branched and can be, for example: methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, icosyl, henicosyl, docosyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1,1,3,3-tetramethylhexyl or 1-methyundecyl.

Examples of $R^6$ and $R^7$ and of advantageous radicals $R^1$ and $R^3$ are alkyl radicals having 1 to 18 C atoms. Examples can be taken analogously from the above list. Alkyl radicals such as ethyl, n-butyl or heptadecyl are preferred.

Long-chain alkyl radicals can be straight-chain or branched and also mixed-chain radicals, and in particular the branched-chain radicals can also be in the form of mixtures of their isomers.

$R^1$ and $R^3$ can also be alkenyl having 2 to 18 C atoms. Examples of these are vinyl, allyl, 2-methallyl, butenyl, e.g. 2-butenyl, hexenyl, e.g. 2-hexenyl, decenyl, undecenyl, e.g. 10-undecenyl, heptadecenyl or oleyl.

Examples of the said unsubstituted cycloalkyl groups $R^1$, $R^3$, $R^6$ and $R^7$ having 5 to 12 C atoms are cyclopentyl, cyclohexyl, cyclooctyl and cyclododecyl, cyclohexyl being particularly preferred. Examples of $C_1$-$C_8$alkyl-substituted cycloalkyl groups having 5 to 12 ring C atoms are those which advantageously carry one, two or three alkyl groups having 1 to 8 C atoms in total, and these can be 2- or 4-methylcyclohexyl, dimethylcyclohexyl, trimethylcyclohexyl or t-butylcyclohexyl.

An unsubstituted or $C_1$-$C_8$alkyl-substituted $C_5$-$C_{12}$cycloalkyl-$C_1$-$C_4$alkyl group $R^1$, $R^3$, $R^6$ and $R^7$ means, for example, radicals of the general formula

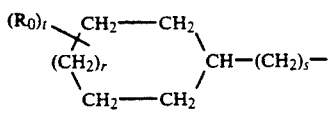

r being one of the numbers 0, 1, 2, 3, 4, 5, 6, or 7, s being one of the numbers 1, 2, 3 or 4 and t being one of the numbers 0 or 1 and higher, advantageously 0, 1, 2 or 3, and $R_o$ being alkyl having 1 to 8 C atoms, preferably methyl, ethyl, propyl, n-butyl or t-butyl.

Radicals of the formulae

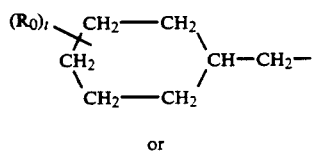

or

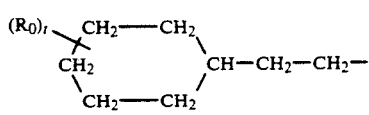

in which $t=0$, 1, 2 or 3 and $R_0$ is methyl or t-butyl and, particularly preferably, $R_0$ being methyl and $t=1$, 2 or 3 or $R_0$ being t-butyl and $t=1$, or t being 0, are advantageous.

The substituents $R_1$, $R_3$, $R_6$ and $R_7$ can also be unsubstituted or $C_1$-$C_8$alkyl-substituted $C_3$-$C_{12}$cycloalkyl groups which are interrupted by one or more groups from the series comprising —O—, —S—, —NH—,

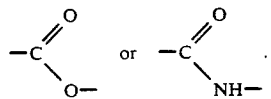

Those radicals of the general formula

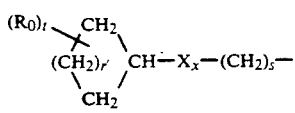

are preferred in which r' is one of the numbers 0 or 1 to 9, but advantageously 3.

X can be one of the groups from the series comprising —O—, —S—, —NH—,

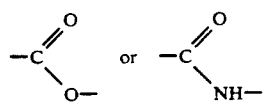

and preferably is

s can be 1, 2, 3 or 4 and is advantageously 1. The definitions of $R_0$ and t and the preferred definitions are given above.

An interruption in the alkyl group by

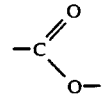

is particularly preferred. The group of the formula

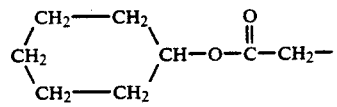

is very particularly preferred.

$C_7$-$C_{18}$Aralkyl $R^1$ or $R^3$ can especially be naphthyl-$C_1$-$C_8$alkyl and in particular phenyl-$C_1$-$C_8$alkyl, for example benzyl, 2-phenylethyl (dihydrostyryl) or methylbenzyl.

Examples of $R^1$ and $R^3$ associated with the $C_7$-$C_{18}$alkaryl radicals include, for example, $C_{11}$-$C_{18}$alkylnaphthyl and especially $C_7$-$C_{18}$alkylphenyl, preferably methylphenyl, dimethylphenyl, trimethylphenyl, ethylphenyl, isopropylphenyl, t-butylphenyl, di-t-butylphenyl or 2,6-di-t-butyl-4-methylphenyl.

The substituent $R^2$ is, for example, —NR$^4$R$^5$, in which $R^4$ and $R^5$ can be identical or different and preferably are identical.

An alkyl radical $R^4$ and $R^5$ having 1 to 23 C atoms can, for example, be methyl, ethyl, n-propyl, i-propyl, n-butyl, i-butyl, n-pentyl, n-hexyl, n-heptyl, n-octyl, 2-ethylhexyl, nonyl, decyl, undecyl, dodecyl, heptadecyl or henicosyl.

Examples of an —NR$^4$R$^5$ radical $R^2$ are the N-butyl, N-hexyl, N-n-octyl, N-t-octyl, N-t-dodecyl, N-t-tetradecyl, N-t-docosyl, N-methyl-N-octyl, N-methyl-N-dodecyl, N-methyl-N-hexadecyl, N-methyl-N-octadecyl, N,N-di-i-butyl, N,N-di-n-hexyl, N,N-di-t-octyl, N,N-di-2-ethylhexyl, N,N-di-dodecyl, N-methyl-N-phenyl or N-dodecyl-N-phenyl radicals.

Moreover, $R^4$ and $R^5$ can be $C_7$-$C_{18}$aralkyl and $C_7$-$C_{18}$alkaryl. Examples of these are to be found in the lists given above.

In a substituent $R^2$ defined as —OR$^6$ or —SR$^7$, $R^6$ and $R^7$ are, for example, alkyl having 1 to 18 C atoms. Examples thereof are methyl, ethyl, propyl, isopropyl, n-butyl isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1,1,3,3-tetramethylhexyl or 1-methylundecyl.

Preferred examples are methyl, ethyl, n-butyl, n-octyl, i-octyl, 2-ethylhexyl and 1,1,3,3-tetramethylhexyl.

Preferred examples of $R^6$ and $R^7$, which are alkyl having 2 to 20 C atoms interrupted by one or more groups from the series comprising —O—, —S—, —NR—,

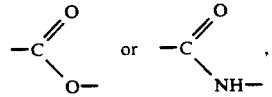

include radicals of the formula

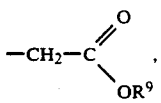

$R^9$ being $C_1$-$C_{18}$alkyl and preferably $C_4$-$C_{12}$alkyl.

Suitable examples of $C_7$-$C_{18}$alkaryl or $C_7$-$C_{18}$aralkyl $R^6$ and $R^7$ can be taken from the above list. A benzyl radical is preferred for $R^6$ and especially for $R^7$.

$R^8$ is, inter alia, defined a alkylene having 1 to 18 C atoms, including methylene, ethylene, trimethylene, 2,2-dimethyl-1,3-propanediyl, tetramethylene, pentamethylene, hexamethylene, heptamethylene, octamethylene, decamethylene or dodecamethylene as examples. Trimethylene, tetramethylene, hexamethylene and octamethylene are preferred.

Examples of alkylene $R^8$ interrupted by 1 or 2 oxygen atoms are 3-oxapentane-1,5-diyl, 3,6-dioxaoctane-1,8-diyl, 2-oxapropane-1,3-diyl, 2,7-dioxaoctane-1,8-diyl or 2,6-dioxa-4,4-dimethyl-1,7-heptanediyl.

$R^8$ can also be alkylidene having 2 to 20 C atoms, examples being ethylidene, propylidene, butylidene, pentylidene, 4-methylpentylidene, heptylidene, nonylidene, tridecylidene, nonadecylidene, 1-methylethylidene and 1-ethylpropylidene.

Examples of $C_1$-$C_{18}$alkyl and especially $C_4$-$C_{12}$alkyl $R^9$ can be taken analogously from the above list of alkyl radicals.

A further example of a preferred group $R^1$ is

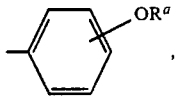

$R^a$ being as defined, and

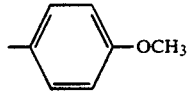

is particularly preferred for $R^1$.

Further advantageous compositions contain a compound of the formula Ia

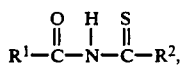

(Ia)

$R^1$ and $R^2$ being as defined above, or a compound of the formula Ib

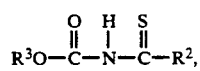

(Ib)

$R^2$ and $R^3$ being as defined above, or a compound of the formula Ic

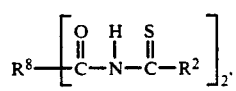

(Ic)

$R^2$ and $R^8$ being as defined above.

The scope of the present invention includes that several compounds of the formula I, respectively Ia, Ib and/or Ic, can also be used in the compositions in any desired mixture with one another.

Particularly advantageous compositions include also those which contain a compound of the formula Ia, in which $R^1$ is alkyl having 1 to 18 C atoms, phenyl or benzyl and $R^2$ is —O—($C_1$-$C_{18}$)alkyl, —N[($C_1$-$C_{18}$)alkyl]$_2$, —O—($C_5$-$C_{12}$)cycloalkyl, —O-phenyl, —O—($C_7$-$C_{18}$)aralkyl, —S—($C_1$-$C_{12}$)alkyl, —S-phenyl, —S—($C_7$-$C_{18}$)aralkyl or —S—$CH_2$—$COOR^9$, $R^9$ being $C_1$-$C_{18}$alkyl.

Another particularly advantageous composition contains a compound of the formula Ib, in which $R^2$ is —O—($C_1$-$C_{18}$)alkyl, —O—($C_5$-$C_{12}$)cycloalkyl, —O-phenyl, —O—($C_7$-$C_{18}$)aralkyl, —S—($C_1$-$C_{12}$)alkyl, —S-phenyl, —S—($C_7$-$C_{18}$)aralkyl or —S—$CH_2$—$COOR^9$, $R^9$ being $C_1$-$C_{18}$alkyl and $R^3$ being $C_1$-$C_{18}$alkyl, cyclohexyl, phenyl or benzyl.

A further particularly advantageous composition contains a compound of the formula Ic, in which $R^2$ is —O—($C_1$-$C_{18}$)alkyl, —N[($C_4$-$C_8$)alkyl]$_2$, —O-phenyl, —O—($C_7$-$C_{18}$)aralkyl, —O—($C_5$-$C_{12}$)cycloalkyl, —S—($C_1$-$C_{12}$)alkyl, —S-phenyl, —S—($C_7$-$C_{18}$)aralkyl or —S—$CH_2$—$COOR^9$, $R^9$ being $C_1$-$C_{18}$alkyl or $C_5$-$C_{12}$cycloalkyl and $R^8$ being $C_1$-$C_{10}$alkylene or $C_2$-$C_{10}$alkylidene.

The preferred compositions also include those which contain a compound of the formula Ia, in which $R^1$ is alkyl having 9 to 18 C atoms or phenyl and $R^2$ is —O—($C_1$-$C_8$)alkyl, —S—($C_8$-$C_{10}$)alkyl, —N[($C_4$-$C_8$)alkyl]$_2$, —S—$CH_2$—COO—($C_2$-$C_8$)alkyl or —S-benzyl, or contain a compound of the formula Ib in which $R^2$ is —O—($C_2$-$C_8$)alkyl, —S—($C_8$-$C_{12}$)alkyl or —N—[($C_4$-$C_8$)alkyl]$_2$ and $R^3$ is $C_2$-$C_4$alkyl, cyclohexyl or phenyl, or contain a compound of the formula Ic, in which $R^2$ is —N[($C_4$-$C_8$)alkyl]$_2$ and $R^8$ is $C_3$-$C_8$alkylene.

Compositions which are particularly preferred contain a compound of the formula Ia, in which $R^1$ is phenyl and $R^2$ is —$SR^7$ or —S—$CH_2$—$COOR^9$ and $R^7$ is $C_4$-$C_{12}$alkyl and $R^9$ is $C_4$-$C_{12}$alkyl, or contain a compound of the formula Ib, in which $R^2$ is —$SR^7$ or —S—$CH_2$—$COOR^9$, $R^7$ being $C_4$-$C_{12}$alkyl and $R^9$ being $C_4$-$C_{12}$alkyl, and $R^3$ is $C_1$-$C_4$alkyl, cyclohexyl or phenyl, or contain a compound of the formula Ib in which $R^2$ is —S-n-octyl and $R^3$ is ethyl or $R^2$ is —S-(2-ethylhexyl) and $R^3$ is n-butyl.

The compounds of the formula I are in some cases known from the literature references cited below, or they can be prepared, for example, by the methods known per se.

Such methods are described in H. Hartmann, I. Reuther, Journal für praktische Chemie, volume 315, no. 1, 1973, pages 144–148; K. H. König, M. Kuge, L. Kaul, M. J. Pletsch, Chemische Berichte 120, pages 1251–1253, (1987), and in E. Schröpl, R. Pohloudek-Fabini, Pharmazeutische Zentralhalle, volume 107, (1968), no. 7, pages 493–500.

In analogy to the methods known per se, the following general equations of the process for preparing the compounds of the formulae Ia and Ib can be given:

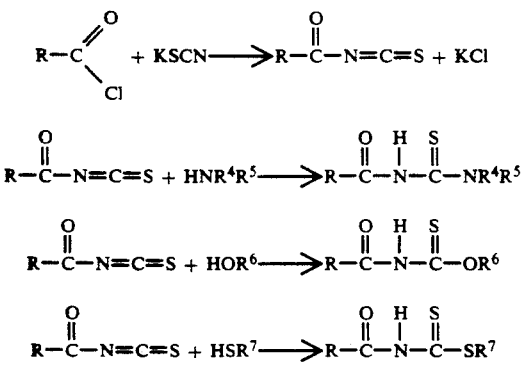

The equation:

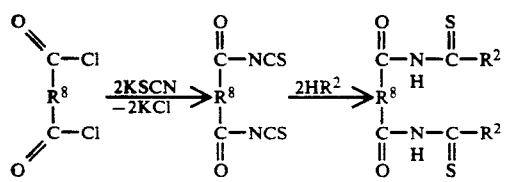

applies, for example, to compounds of the formula Ic. The symbols R, $R^2$, $R^4$, $R^5$, $R^6$, $R^7$ and $R^8$ can be as defined above.

The starting materials, for example an acyl chloride, a thiocyanate and the selected amine, the alcohol or the phenol or the mercaptan or thiophenol are reacted, for example in a polar aprotic solvent, at temperatures between about 50° C. and 70° C.

The thiocyanate can also be reacted in a first process stage with a halogenoformate. Examples of such esters are methyl chloroformate (chloroformic acid methyl ester), ethyl chloroformate, allyl chloroformate, benzyl chloroformate, butyl chloroformate, phenyl chloroformate or vinyl chloroformate.

Suitable acyl chlorides can be devised analogously from the above definitions for R, and examples of these are acetyl chloride, butyryl chloride, oleoyl chloride, 3-phenylpropionyl chloride and benzoyl chloride or, for $R^8$, glutaric acid dichloride, adipic acid dichloride, suberic acid dichloride, sebacic acid dichloride etc.

Ammonium thiocyanate, sodium thiocyanate and preferably potassium thiocyanate can be listed as examples of thiocyanates.

Corresponding to the definitions of $R^2$ or $R^4$, $R^5$, $R^6$ and $R^7$ respectively, the amines can be, for example, n-butylamine, 2-ethylhexylamine, dihexylamine, bis-(2-ethylhexyl)amine, methylaniline, piperidine, morpholine, hexamethylenimine (perhydroazepine), pyrrolidine, 1-methylpiperazine and piperazine, examples of alcohols or phenols are ethanol, butanol, iso-butanol, 2-ethylhexanol, cyclohexanol, phenol and 4-methylphenol (p-cresol), and mercaptans or thiophenols are, for example, octylmercaptan, tert-dodecylmercaptan, ethyl thioglycolate, 2-ethylhexyl thioglycolate or 3,5-dimethylthiophenol etc.

The listing of starting materials represents examples. The complete starting materials result analogously and correspondingly from all the possible substituents R and $R^2$.

The compositions according to the invention contain a lubricant or a hydraulic fluid as a further component. Lubricants are preferred, and the products known per se can be used.

The desired properties of the compounds according to the invention also fully manifest themselves in the hydraulic fluids, although in this case a low level of or freedom from ash and phosphorus is not of such great importance as mentioned above.

The relevant lubricants and hydraulic fluids are known to those skilled in the art and are described, for example, in Dieter Klamann "Schmierstoffe und verwandte Produkte [Lubricants and related products]", Verlag Chemie, Weinheim, 1982, in Schewe-Kobek, "Das Schmiermittel-Taschenbuch [The Lubricants Handbook]", Dr. Alfred Hüthig-Verlag, Heidelberg, 1974, or in "Ullmanns Encyclopädie der technischen Chemie [Ullmann's Encylopaedia of Industrial Chemistry]", volume 13, pages 85-94 (Verlag Chemie, Weinheim, 1977).

Examples are lubricants and hydraulic fluids based on mineral oils, synthetic oils or mixtures of mineral and synthetic oils, or synthetic lubricants or hydraulic fluids, for example those which are carboxylic ester derivatives and can be used at temperatures of 200° C. and higher.

Examples of synthetic lubricants also include lubricants based on a diester of a dibasic acid with a monohydric alcohol, for example dioctyl sebacate or dinonyl adipate, a triester of trimethylolpropane with a monobasic acid or with a mixture of such acids, for example trimethylolpropane tripelargonate, trimethylolpropane tricaprylate or mixtures thereof, a tetraester of pentaerythritol with a monobasic acid or with a mixture of such acids, for example pentaerythritol tetracaprylate, or a complex ester of monobasic and dibasic acids with polyhydric alcohols, for example a complex ester of trimethylolpropane with caprylic and sebacic acids or a mixture thereof.

For example poly-α-olefins, ester-based lubricants, phosphates, glycols, polyglycols and polyalkylene glycols and mixtures thereof with water are particularly suitable in addition to mineral oils.

The compounds of the formula I are readily soluble in lubricants and hydraulic fluids and are therefore particularly suitable as additives to lubricants and hydraulic fluids, and their suprisingly good antioxidant action and wear-reducing action are to be emphasized.

For example in lubricants for internal combustion engines, such as internal combustion engines operating on the spark ignition principle, the compounds of the formula I are able to deploy their outstanding properties. Thus, the compounds of the formula I in lubricating oils prevent or reduce the frictional wear of metal components and have an antioxidant action in the lubricating oil, but without adversely affecting a catalytic exhaust gas purification system.

The compounds of the formula I are active even in very small quantities as additives in lubricants and hydraulic fluids. Advantageously, they are admixed to the lubricants and hydraulic fluids in a quantity of 0.01 to 5% by weight, preferably in a quantity of 0.05 to 3% by weight and very particularly preferably in a quantity of 0.1 to 2% by weight, in each case relative to the lubricant or hydraulic fluid.

The lubricants and hydraulic fluids according to the invention can additionally contain other additives, which are added for yet further improvement in the base properties of lubricants and hydraulic fluids; these include: further antioxidants, metal deactivators, rust inhibitors, viscosity index improvers, pour-point depressants, dispersants, detergents, surfactants, further extreme-pressure additives and anti-wear additives.

A number of such compounds is shown by way of example in the list which follows.

EXAMPLES OF PHENOLIC ANTIOXIDANTS

1. Alkylated monophenols 2,6-Di-tert-butylphenol, 2,6-di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butyl-phenol, 2,6-di-tert-butyl-4-iso-butylphenol, 2,6-di-cyclopentyl-4-methylphenol, 2(α-methylcyclohexyl)-4,6-dimethylphenol, 2,6-di-octadecyl-4-methylphenol, 2,4,6-tri-cyclo-hexylphenol, 2,6-di-tert-butyl-4-methoxymethylphenol and o-tert-butylphenol.

2. Alkylated hydroquinones 2,6-Di-tert-butyl-4-methoxyphenol, 2,5-di-tert-butylhydroquinone, 2,5-di-tert-amyl-hydroquinone and 2,6-diphenyl-4-octadecyloxyphenol.

3. Hydroxylated thiodiphenyl ethers 2,2'-Thio-bis-(6-tert-butyl-4-methylphenol), 2,2'-thio-bis-(4-octylphenol), 4,4'-thio-bis-(6-tert-butyl-3-methylphenol) and 4,4'-thio-bis-(6-tert-butyl-2-methylphenol).

4. Alkylidene-bisphenols 2,2'-Methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methyl-phenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-iso-butylphenol), 2,2'-methylene-bis-[6-(α-methylbenzyl)-4-nonylphenol], 2,2'-methylene-bis-[6-(α,α-di-methylbenzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methylphenyl)-3-n-dodecyl-mercaptobutane, ethylene glycol bis-[3,3-bis-(3'-tert-butyl-4'-hydroxyphenyl)-butyrate], bis-(3-tert-butyl-4-hydroxy-5-methylphenyl)-di-cyclopentadiene and bis-[2-(3'-tert-butyl-2'-hydroxy-5'-methyl-benzyl)-6-tert-butyl-4-methyl-phenyl]terephthalate.

5. Benzyl compounds 1,3,5-Tri-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercaptoacetate, bis-(4-tert-butyl-3-hydroxy-2,6-dimethylbenzyl)dithiol-terephthalate, 1,3,5-tris-(3,5-di-tert-butyl-4-hydroxybenzyl)isocyanurate, 1,3,5-tris-(4-tert-butyl-3-hydroxy-2,6-di-methylbenzyl)isocyanurate, di-octadecyl 3,5-di-tert-butyl-4-hydroxybenzylphosphonate and the calcium salt of monoethyl 3,5-di-tert-butyl-4-hydroxybenzylphosphonate.

6. Acylaminophenols

Lauric acid 4-hydroxyanilide, stearic acid 4-hydroxyanilide, 2,4-bis-octylmercapto-6-(3,5-di-tert-butyl-4-hydroxyanilino)-s-triazine and octyl N-(3,5-di-tert-butyl-4-hydroxyphenyl)-carbamate.

7. Esters of β-(3,5-di-tert-butyl-4-hydroxyphenyl)-propionic acid with monohydric or polyhydric alcohols, for example with methanol, diethylene glycol, octadecanol, triethylene glycol, 1,6-hexanediol, pentaerythritol, neopentyl glycol, tris-hydroxyethyl isocyanurate, thiodiethylene glycol and bis-hydroxyethyl-oxamide.

8. Esters of β-(5-tert-butyl-4-hydroxy-3-methylphenyl)-propionic acid with monohydric or polyhydric alcohols, for example with methanol, diethylene glycol, octadecanol, triethylene glycol, 1,6-hexanediol, pentaerythritol, neopentyl glycol, tris-hydroxyethyl isocyanurate, thiodiethylene glycol and bis-hydroxyethyl-oxamide.

9. Amides of β-(3,5-di-tert-butyl-4-hydroxyphenyl)-propionic acid for example N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydrophenylpropionyl)-hydrazine.

Examples of amine-type antioxidants:

N,N'-Di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methylpentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)-amine, 2,6-di-tert-butyl-4-dimethylamino-methylphenol, 2,4'-di-amino-diphenylmethane, 4,4'-diaminodiphenylmethane, N,N,N',N'-tetramethyl-4,4'-diaminodiphenylmethane, 1,2-di-[(2-methyl-phenyl)-amino]-ethane, 1,2-di-(phenylamino)-propane, (o-tolyl)-biguanide, di-[4-(1',3'-dimethylbutyl)-phenyl]-amine, tert-octylated N-phenyl-1-naphthylamine, a mixture of monoalkylated and dialkylated tert-butyl-/tert-octyl-diphenylamines, 2,3-dihydro-3,3-dimethyl-4H-1,4-benzothiazine, phenothiazine and N-allylphenothiazine.

Examples of further antioxidants

Aliphatic or aromatic phosphites, esters of thiodipropionic acid or thiodiacetic acid, or salts of dithiocarbamic acid or dithiophosphoric acid.

Examples of metal deactivators, for example for copper

Triazoles, benzotriazoles and derivatives thereof, 2-mercaptobenzotolutriazoles and derivatives thereof, 2-mercaptobenzothiazole, 2-mercaptobenzotriazole, 2,5-dimercaptobenzotriazole, 2,5-di-mercaptobenzothiadiazole, 5,5'-methylenebisbenzotriazole, 4,5,6,7-tetrahydrobenzotriazole, salicylidene-propylenediamine, salicylaminoguanidine and salts thereof, diethanolaminomethyltolytriazole and di-(2-ethylhexyl)-aminomethyltolyltriazole.

Examples of rust inhibitors a) Organic acids and esters, metals salts and anhydrides thereof, for example:

N-oleoyl-sarcosine, sorbitan monooleate, lead naphthenate, alkenylsuccinic anhydride, for example dodecenylsuccinic anhydride, partial esters and amides of alkenylsuccinic acids, and 4-nonyl-phenoxy-acetic acid.

b) Nitrogen-containing compounds, for example:
I. Primary, secondary or tertiary aliphatic or cycloaliphatic amines and amine salts of organic and inorganic acids, for example oil-soluble alkylammonium carboxylates.
II. Heterocyclic compounds, for example: Substituted imidazolines and oxazolines.

c) Phosphorus-containing compounds, for example:
Amine salts of partial esters of phosphoric or phosphonic acids, and zinc dialkyl dithiophosphates.

d) Sulfur-containing compounds, for example:
Barium dinonylnaphthalenesulfonates and calcium petroleum-sulfonates.

Examples of viscosity index improvers
Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants
Polymethacrylate and alkylated napthalene derivatives.

Examples of dispersants/surfactants
Polybutenyl-succinamides or succinimides, polybutenylphosphonic acid derivatives and basic magnesium, calcium and barium sulfonates and phenolates.

Examples of anti-wear additives and extreme-pressure additives
Compounds containing sulfur and/or phosphorus and/or halogen, such as sulfurated vegetable oils, zinc dialkyl dithiophosphates, tritolyl phosphate, chlorinated paraffins, alkyl sulfides, aryl disulfides and trisulfides, and triphenyl phosphorothionates.

Some of the compounds which can be used according to the invention are novel. The present invention therefore also relates to novel compounds of the general formula II

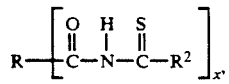

in which $x = 1$ or 2,
$R^2$ is as defined for $-OR^6$ or $-SR^7$ and,
if $x = 1$,
R is as defined for $R^1$ or $R^3-O-$,
and $R^1$ is alkyl having 1 to 25 C atoms, an unsubstituted or $C_1-C_8$alkyl-substituted cycloalkyl group having 5 to 12 ring C atoms, an unsubstituted or $C_1-C_8$alkyl-substituted $C_5-C_{12}$cycloalkyl-$C_1-C_4$alkyl group, alkenyl having 2 to 18 C atoms, phenyl, naphthyl, $C_7-C_{18}$aralkyl or $C_7-C_{18}$alkaryl, or
$R^3$ is alkyl having 9 to 25 C atoms, an unsubstituted or $C_1-C_8$alkyl-substituted cycloalkyl group having 5 to 12 ring C atoms, an unsubstituted or $C_1-C_8$alkyl-substituted $C_5-C_{12}$cycloalkyl-$C_1-C_4$alkyl group, alkenyl having 5 to 18 C atoms, $C_7-C_{18}$aralkyl or $C_7-C_{18}$alkaryl, or
$R^1$ and $R^3$ are alkyl having 1 to 25 C atoms, an unsubstituted or $C_1-C_8$alkyl-substituted cycloalkyl group having 5 to 12 ring C atoms, an unsubstituted or $C_1-C_8$alkyl-substituted $C_5-C_{12}$cycloalkyl-$C_1-C_4$alkyl group, alkenyl having 2 to 18 C atoms, phenyl, naphthyl, $C_7-C_{18}$aralkyl or $C_7-C_{18}$alkaryl, each of which are monosubstituted or polysubstituted by groups from the series comprising halogen, cyano, nitro, $-OR^a$ or $-COOR^b$, or $R^1$ and $R^3$ are alkyl having 2 to 25 C atoms, an unsubstituted or $C_1-C_8$alkyl-substituted cycloalkyl group having 3 to 10 ring C atoms, an unsubstituted or $C_1-C_8$alkyl-substituted $C_3-C_{12}$cycloalkyl-$C_1-C_4$alkyl group, alkenyl having 3 to 18 C atoms, $C_7-C_{18}$aralkyl or $C_7-C_{18}$alkaryl, each of which are interrupted by one or more groups from the series comprising $-O-$, $-S-$, $-NH-$,

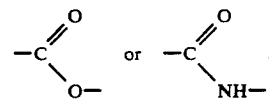

$C_7-C_{18}$aralkyl or $C_7-C_{18}$alkaryl being interrupted only in the alkyl radicals, or
$R^1$ and $R^3$ are alkyl having 2 to 25 C atoms, an unsubstituted or $C_1-C_8$alkyl-substituted cycloalkyl group having 3 to 10 ring C atoms, an unsubstituted or $C_1-C_8$alkyl-substituted $C_3-C_{12}$cycloalkyl-$C_1-C_4$alkyl group, alkenyl having 3 to 18 C atoms, $C_7-C_{18}$aralkyl or $C_7-C_{18}$alkaryl, each of which are monosubstituted or polysubstituted by groups from the series comprising halogen, cyano, nitro, $-OR^a$ or $-COOR^b$ and interrupted by one or more groups from the series comprising $-O-$, $-S-$, $-NH-$,

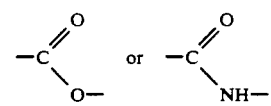

$C_7-C_{18}$aralkyl or $C_7-C_{18}$alkaryl being interrupted only in the alkyl radicals,
$R^a$ being as defined for $R^3$ with the exception of $-OR^a$ and
$R^b$ being alkyl having 1 to 18 C atoms or alkyl having 2 to 20 C atoms and interrupted by one or more groups from the series comprising $-O-$, $-S-$, $-NH-$,

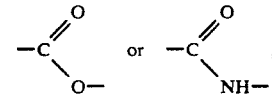

or an unsubstituted or $C_1-C_8$alkyl-substituted cycloalkyl group having 5 to 12 ring C atoms or phenyl, naphthyl, $C_7-C_{18}$alkaryl or $C_7-C_{18}$aralkyl, and $R^6$ and $R^7$ are alkyl having 11 to 18 C atoms or alkyl having 2 to 20 C atoms and interrupted by one or more groups from the series comprising $-O-$, $-S-$, $-NH-$,

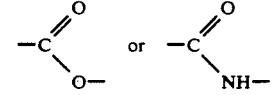

or an unsubstituted or $C_1-C_8$alkyl-substituted cycloalkyl group having 5 to 12 ring C atoms, an unsubstituted or $C_1-C_8$alkyl-substituted $C_5-C_{12}$cycloalkyl-$C_1-C_4$alkyl group, an unsubstituted or $C_1-C_8$alkyl-substituted $C_3-C_{12}$cycloalkyl-$C_1-C_4$alkyl group interrupted by one or more groups from the series comprising $-O-$, $-S-$, $-NH-$,

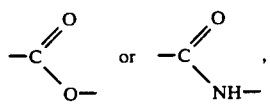

$C_7$-$C_{18}$alkaryl or $C_7$-$C_{18}$aralkyl, or,
if $x=2$,
R is as defined for $R^8$ and
$R^8$ is alkylene having 1 to 18 C atoms, alkylene having 2 to 18 C atoms and interrupted by at least one —O— group, alkylidene having 2 to 20 C atoms or alkylidene having 3 to 20 C atoms and interrupted by at least one —O— group.

In the above definitions, the expressions "one or more groups" or "by at least one group" mean, for example, one, two or three groups, one group being preferred.

For alkyl $R^3$, alkyl groups having 10 to 25 C atoms are advantageous, alkyl groups having 12 to 25 C atoms are preferred and alkyl groups having 15 to 18 C atoms are particularly preferred.

For alkenyl $R^3$, alkenyl groups having 8 to 18 C atoms are advantageous and alkenyl groups having 12 to 18 C atoms are preferred.

For alkyl $R^6$, alkyl groups having 12 to 18 C atoms are advantageous and alkyl groups having 15 to 18 C atoms are preferred.

Advantageous compounds are of the formula IIa

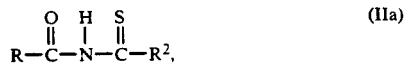

in which R is as defined for $R^1$ or $R^3$—O— and $R^1$, $R^2$ and $R^3$ are as defined above.

Further advantageous compounds are of the formula IIc

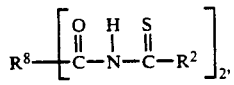

in which $R^2$ and $R^8$ are as defined above.

Preferred compounds are of the formula IIa, in which R is as defined for $R^1$ or —O—$R^3$ and $R^1$ is phenyl or alkyl having 1 to 18 C atoms and $R^3$ is alkyl having 1 to 18 C atoms or phenyl, and $R^2$ is —$SR^7$.

In particularly preferred compounds of the formula IIa, $R^2$ is —$SR^7$, $R^7$ being alkyl having 1 to 18 C atoms,

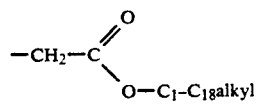

or phenyl-$C_1$-$C_4$alkyl.

Particularly preferred compounds are of the formulae

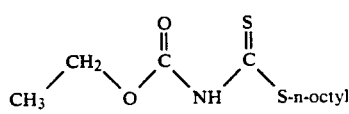

-continued
or

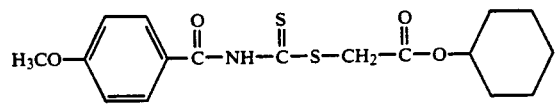

The present invention also relates to the use of the compounds of the formulae I and II as anti-wear additives, for example in lubricants, for metal components which are subject to frictional wear, and as antioxidants in lubricants.

The invention is explained in more detail by reference to the examples which follow. All data in percentages or parts are by weight, unless otherwise stated.

EXAMPLE 1

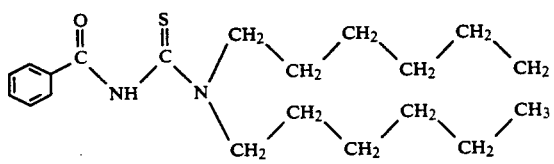

14.35 g (0.1 mole) of benzoyl chloride are added dropwise in the course of 15 minutes to a solution of 9.9 g (0.1 mole) of potassium thiocyanate in 100 ml of acetone at reflux temperature. After stirring for a further 30 minutes under reflux, 18.9 g (0.1 mole) of dihexylamine are added dropwise under reflux in the course of 20 minutes to the suspension which is now white. After a further 5 hours under reflux, the reaction mixture is poured onto 400 ml of 10% hydrochloric acid and extracted with toluene and ethyl acetate. The organic phase is dried with magnesium sulfate and evaporated. The crude product is eluted through a little silica gel (toluene: ethyl acetate 4:1). After removal of the solvent, this gives 22.3 g of a brown-orange oil (64% of theory).

EXAMPLE 12

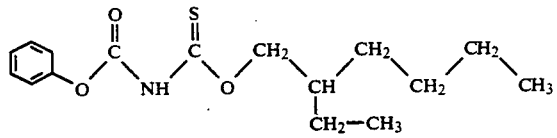

11.1 g (0.07 mole) of phenyl chloroformate are added dropwise in the course of 30 minutes at 50° to a supersaturated solution of 6.9 g (0.07 mole) of potassium thiocyanate in 80 ml of ethyl acetate. The yellow suspension is stirred for a further 90 minutes at 60°. 9.2 g (0.07 mole) of 2-ethyl-1-hexanol are then added dropwise at the same temperature. The mixture is stirred for a further 20 hours at 60°-65°. 40 ml of water are then added, and the emulsion cooled to room temperature is separated in a separating funnel. The organic phase is dried over magnesium sulfate and evaporated. The crude product is eluted over a short silica gel column as described before: yield 12.3 g (57% of theory).

Examples 2 to 11 and 13 to 26 are carried out analogously to Examples 1 and 12, as shown in the Table. The method chosen is indicated in detail for in each case.

| Example No. | Compound | Method according to Example | Yield (% of theory) | Appearance | ¹H-NMR absorption of the group CONHCS (O=C-NH-C=S) [CDCl₃, ppm] | Analysis C | Calculated Found H | N | [%] S |
|---|---|---|---|---|---|---|---|---|---|
| 1 | (benzoyl thiourea with long alkyl chain) | 1 | 64 | red-brown oil | 8.5 | 68.92 69.27 | 9.25 8.04 9.29 7.77 | | 13.77 13.66 |
| 2 | (benzoyl thiourea with diisobutyl pyrrolidine) | 1 | 96 | orange-brown powder, melting point 124–126 | 8.4 | 65.71 65.75 | 8.27 9.58 8.25 9.47 | | 10.96 10.95 |
| 3 | (benzoyl thiourea with branched long alkyl) | 12 | 81 | orange-brown oil | 8.4 | 71.24 71.47 | 9.96 6.92 9.80 6.82 | | 7.92 7.98 |
| 4 | (benzoyl thiocarbamate methyl) | 1 | | white powder, melting point 94 | 9.2 | 55.37 55.72 | 4.65 7.17 4.81 6.97 | | 16.42 16.14 |
| 5 | (benzoyl thiocarbamate butyl) | 1 | 61 | yellow powder, melting point 46–48 | 9.25 | 60.73 61.18 | 6.37 5.90 6.49 5.73 | | 13.51 13.46 |
| 6 | (benzoyl thiocarbamate 2-ethylhexyl) | 1 | 76 | yellow oil | 9.2 | 65.49 65.60 | 7.90 4.77 7.95 4.97 | | 10.93 11.00 |

-continued

| Example No. | Compound | Method according to Example | Yield (% of theory) | Appearance | ¹H-NMR absorption of the group CONHCS [CDCl₃, ppm] | Analysis C | Calculated Found H | N | [%] S |
|---|---|---|---|---|---|---|---|---|---|
| 7 | benzoyl-NH-C(=S)-S-nonyl | 1 | 93 | yellow resin | 10.1 | 62.10 62.35 | 7.49 7.62 | 4.53 4.51 | 20.72 20.55 |
| 8 | benzoyl-NH-C(=S)-S-(2-ethylhexyl) | 1 | 67 | orange-yellow oil | 10.05 | 62.10 61.97 | 7.49 7.60 | 4.53 4.55 | 20.72 20.61 |
| 9 | benzoyl-NH-C(=S)-S-tert-alkyl | 1 | 48 | orange oil | 9.6 | 63.12 63.04 | 7.79 7.68 | 4.33 4.34 | 19.82 19.32 |
| 10 | benzoyl-NH-C(=S)-S-CH₂-C(=O)-O-(2-ethylbutyl) | 1 | 62 | yellow powder, melting point 72–74 | 10.1 | 59.81 59.86 | 7.13 7.16 | 3.67 3.71 | 16.81 16.59 |
| 11 | benzoyl-NH-C(=S)-S-CH₂-C(=O)-O-ethyl | 1 | 53 | yellow powder, melting point 124–125 | 10.2 | 50.87 50.83 | 4.62 4.63 | 4.94 4.90 | 22.63 22.83 |
| 12 | phenyl-O-C(=O)-NH-C(=S)-O-(2-ethylhexyl) | | 57 | yellow oil | 8.5 | 62.11 62.36 | 7.49 7.63 | 4.53 4.46 | 10.36 10.25 |

-continued

| Example No. | Compound | Method according to Example | Yield (% of theory) | Appearance | ¹H-NMR absorption of the group CONHCS [CDCl₃, ppm] | Analysis C | Calculated Found H | N | [%] S |
|---|---|---|---|---|---|---|---|---|---|
| 13 | (structure) | 12 | 21 | reddish oil | 9.3 | | | | |
| 14 | (structure) | 1 | 37 | yellow oil | 7.2 | 64.47 65.94 | 10.82 7.52 11.14 7.63 | 6.82 | 8.60 8.19 |
| 15 | (structure) | 1 | 65 | yellow oil | 8.5 | 46.81 47.00 | 7.37 6.82 7.52 6.79 | | 15.62 15.67 |
| 16 | (structure) | 12 | 84 | yellow resin | 9.2 | 51.95 53.01 | 8.36 5.05 8.44 4.85 | | 23.11 22.39 |
| 17 | (structure) | 1 | 62 | orange powder, melting point 89–90 | 9.1 | 38.23 38.15 | 5.21 5.57 5.13 5.97 | | 25.51 25.61 |
| 18 | (structure) | 1 | 62 | yellow oil | 9.1 | 50.12 49.75 | 7.51 4.18 7.48 4.23 | | 19.11 19.02 |
| 19 | (structure) | 12 | 88 | yellowish oil | 8.3 | 58.10 58.18 | 9.40 4.84 9.33 4.77 | | 11.08 11.15 |

-continued

| Example No. | Compound | Method according to Example | Yield (% of theory) | Appearance | ¹H-NMR absorption of the group CONHCS [CDCl₃, ppm] | Analysis C | Calculated Found H | N | [%] S |
|---|---|---|---|---|---|---|---|---|---|
| 20 | (structure: alkyl-O-C(O)-NH-C(S)-S-alkyl branched) | 12 | 74 | yellow oil | 9.1 | 55.04 55.13 | 8.91 8.96 4.59 4.54 | 4.59 4.54 | 20.99 20.93 |
| 21 | C₁₇H₃₃-C(O)-NH-C(S)-S-alkyl | 12 | 70 | yellow liquid | 9.55 | 69.02 69.27 | 10.94 10.85 2.98 2.82 | 2.98 2.82 | 13.65 13.34 |
| 22 | C₁₇H₃₃-C(O)-NH-C(S)-S-CH₂-C₆H₅ | 12 | 31 | yellow oil | 9.5 | 69.75 69.81 | 9.23 9.38 3.13 3.00 | 3.13 3.00 | 14.32 13.78 |
| 23 | [–(CH₂)₃–C(O)–NH–C(S)–N(alkyl)₂]₂ | 1 | 65 | yellow viscose oil | 9.5 broad | 67.19 67.24 | 10.99 10.83 8.04 7.92 | 8.04 7.92 | 9.20 9.43 |
| 24 | [–(CH₂)₄–C(O)–NH–C(S)–N(alkyl)₂]₂ | 1 | 75 | yellow resin | 8.45 | 67.55 67.54 | 11.05 11.27 7.88 7.73 | 7.88 7.73 | 9.02 9.06 |

-continued

| Example No. | Compound | Method according to Example | Yield (% of theory) | Appearance | ¹H-NMR absorption of the group CONHCS-NH-CH(S)- [CDCl₃, ppm] | Analysis C | Calculated Found H | N | [%] S |
|---|---|---|---|---|---|---|---|---|---|
| 25 | [structure with (CH₂)₆]₂ | 1 | 79 | yellow resin | 8.75 | 68.24 68.42 | 11.18 7.58 10.83 7.56 | | 8.67 8.70 |
| 26 | [structure with (CH₂)₈]₂ | 1 | 88 | orange resin | 8.4 | 68.87 69.19 | 11.30 7.30 11.20 7.22 | | 8.36 8.38 |

EXAMPLE 27

Test For Wear Protection

The suitability as anti-wear additive is tested by the ASTM Standard Method D-2783-81, using the Shell four-ball apparatus. The base oil used is Catenex® P941 made by Shell, to which the quantity, indicated in the table, of compound according to the particular example is added. The following are determined:
a) The weld load WL as the load (in kg) at which the 4 balls weld together within 10 seconds, and
b) the mean wear scar diameter at a load of 40 kg for 1 hour (in mm).

| Compound from Example | Quantity added (% by weight) | Weld load (kg) | Wear scar diameter (mm) |
|---|---|---|---|
| 1 | 0.25 | — | 0.49 |
|   | 1 | 1800 | 0.50 |
| 2 | 0.25 | — | 0.51 |
|   | 1 | 1800 | 0.51 |
| 3 | 0.25 | — | 0.55 |
|   | 1 | 1800 | 0.50 |
| 4 | 0.25 | — | 0.53 |
|   | 1 | 2000 | 0.58 |
|   | 2.5 | 2400 | — |
| 5 | 0.25 | — | 0.53 |
|   | 1 | 2200 | 0.53 |
|   | 2.5 | 2400 | — |
| 6 | 0.25 | — | 0.53 |
|   | 1 | 2000 | 0.51 |
|   | 2.5 | 2400 | — |
| 7 | 0.25 | — | 0.52 |
|   | 1.0 | 2000 | 0.56 |
|   | 2.5 | 2200 | — |
| 8 | 0.25 | — | 0.50 |
|   | 1.0 | 2000 | 0.55 |
|   | 2.5 | 2200 | — |
| 9 | 0.25 | — | 0.52 |
|   | 1.0 | 2200 | 0.50 |
|   | 2.5 | 2400 | — |
| 10 | 0.25 | — | 0.53 |
|    | 1.0 | 1800 | 0.56 |
| 11 | 0.25 | — | 0.57 |
|    | 1.0 | 2200 | 0.59 |
| 12 | 0.25 | — | 0.48 |
|    | 1.0 | 2000 | 0.49 |
|    | 2.5 | 2000 | — |
| 13 | 0.25 | — | 0.49 |
|    | 1.0 | 2000 | 0.54 |
|    | 2.5 | 2200 | — |
| 14 | 0.25 | — | 0.55 |
|    | 1.0 | 1800 | 0.57 |
| 15 | 0.25 | — | 0.51 |
|    | 1.0 | 2200 | 0.58 |
|    | 2.5 | 2400 | — |
| 16 | 0.25 | — | 0.56 |
|    | 1.0 | 2000 | 0.63 |
|    | 2.5 | 2400 | — |
| 17 | 0.25 | — | 0.62 |
|    | 1.0 | 2200 | — |
| 18 | 0.25 | — | 0.58 |
|    | 1.0 | 2200 | 0.65 |
|    | 2.5 | 2800 | — |
| 19 | 0.25 | — | 0.53 |
|    | 1.0 | 2000 | 0.57 |
|    | 2.5 | 2000 | — |
| 20 | 0.25 | — | 0.54 |
|    | 1.0 | 2000 | 0.61 |
|    | 2.5 | 2400 | — |
| 21 | 0.25 | — | 0.67 |
|    | 1.0 | 1800 | 0.45 |
| 22 | 0.25 | — | 0.45 |
|    | 1.0 | 2000 | 0.50 |
|    | 2.5 | 2400 | — |
| 23 | 0.25 | — | 1.51 |
|    | 1.0 | 1800 | 0.52 |
| 24 | 0.25 | — | 0.53 |
|    | 1.0 | 1800 | 0.54 |
| 25 | 0.25 | — | 0.52 |
|    | 1.0 | 1800 | 0.53 |
| 26 | 0.25 | — | 0.51 |
|    | 1.0 | 1800 | 0.54 |
| Reference | without additive | 1400 | 0.70 |

EXAMPLE 28

Test for Stabilization Against Oxidative Degradation (TFOUT: Thin Film Oxygen Uptake Test)

This test is a modified form of the rotary bomb test for mineral oils (ASTM D 2272). A detailed description is to be found in C. S. Ku and S. M. Hsu, Lubrication Engineering 40, (1984), pages 75–83. The test oil in this test is a commercial 15W40 engine oil, with about half the usual content of zinc dithiophosphate (0.75% of ZnDTP, 550 ppm of P, 1160 ppm of Zn). The additive under test is tested in the oil for its stabilizing action in the presence of water (2%), an oxidized/nitrated gasoline fraction (4%) and a mixture of liquid metal naphthenates (4%) at 610 kPa oxygen pressure and 160° C. The water and the two liquid catalysts for the test are obtained under the description Standard Reference Material 1817 from the National Bureau of Standards (NBS), with a certificate for the analysis. The test is complete when a marked break in the pressure/time diagram indicates the start of oxidation at the end of the induction period (minutes).

A long induction period means a good stabilizing action of the additive.

| Compound from Example | Quantity added (% by weight) | Induction period (minutes) |
|---|---|---|
| 5 | 0.5 | 107 |
| 6 | 0.5 | 109 |
| 7 | 0.5 | 123 |
| 9 | 0.5 | 126 |
| 15 | 0.5 | 117 |
| 16 | 0.5 | 129 |
| Reference | without additive | 83 |

What is claimed is:

1. A composition comprising
(a) a lubricant or hydraulic fluid, and
(b) at least one compound of formula Ia

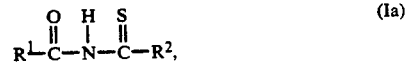

$R^1$ is alkyl having 1 to 25 C atoms, an unsubstituted or $C_1$–$C_8$alkyl-substituted cycloalkyl group having 5 to 12 ring C atoms, an unsubstituted or $C_1$–$C_8$alkyl-substituted $C_5$–$C_{12}$cycloalkyl-$C_1$–$C_4$alkyl group, alkenyl having 2 to 18 C atoms, phenyl, naphthyl, $C_7$–$C_{18}$aralkyl or $C_7$–$C_{18}$alkaryl, or $R^1$ is alkyl having 1 to 25 C atoms, an unsubstituted or $C_1$–$C_8$alkyl-substituted cycloalkyl group having 5 to 12 ring C atoms, an unsubstituted or $C_1$–$C_8$alkyl-substituted $C_5$–$C_{12}$cycloalkyl-$C_1$–$C_4$alkyl group, alkenyl having 2 to 18 C atoms, phenyl, naphthyl, $C_7$–$C_{18}$aralkyl or $C_7$–$C_{18}$alkaryl, each of which are monosubstituted or polysubstituted by group from the series comprising halogen, cyano, nitro, —OR$^a$ or —COOR$^b$, or R$^1$ is alkyl having 2 to 25 C atoms, an unsubstituted or C$_1$-C$_8$alkyl-substituted cycloalkyl group having 3 to 10 ring C atoms, an unsubstituted or C$_1$-C$_8$alkyl-substituted C$_3$-C$_{12}$cycloalkyl-C$_1$-C$_4$alkyl group, alkenyl having 3 to 18 C atoms, C$_7$-C$_{18}$aralkyl or C$_7$-C$_{18}$alkaryl, each of which are interrupted by one or more groups from the series comprising —O—, —S—, —NH—,

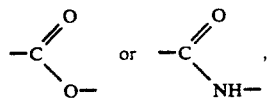

C$_7$-C$_{18}$aralkyl or C$_7$-C$_{18}$alkaryl being interrupted only in the alkyl radicals, or R$^1$ is alkyl having 2 to 25 C atoms, an unsubstituted or C$_1$-C$_8$alkyl-substituted cycloalkyl group having 3 to 10 ring C atoms, an unsubstituted or C$_1$-C$_8$alkyl-substituted C$_3$-C$_{12}$cycloalkyl-C$_1$-C$_4$alkyl group, alkenyl having 3 to 18 C atoms, C$_7$-C$_{18}$aralkyl or C$_7$-C$_{18}$alkaryl, each of which are monosubstituted or polysubstituted by groups from series comprising halogen, cyano, nitro, —OR$^a$ or —COOR$^b$ and are each interrupted by one or more groups from the series comprising —O—, —S—, —NH—,

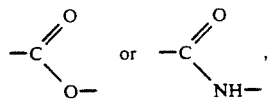

the C$_7$-C$_{18}$aralkyl or C$_7$-C$_{18}$alkaryl being interrupted only in the alkyl radicals, R$^a$ being as defined for R$^1$ with the exception of R$^a$ and R$^b$ being as defined for R$^6$, and R$^2$ is —NR$^4$R$^5$, —OR$^6$ or —SR$^7$, and R$^4$ and R$^5$ are identical or different and are —H, alkyl having 1 to 23 C atoms, an unsubstituted or C$_1$-C$_8$alkyl-substituted cycloalkyl group having 5 to 12 ring C atoms, an unsubstituted or C$_1$-C$_8$alkyl-substituted C$_5$-C$_{12}$cycloalkyl-C$_1$-C$_4$alkyl group, phenyl, naphthyl, C$_7$-C$_{18}$aralkyl or C$_7$-C$_{18}$alkaryl, or R$^4$ and R$^5$, together with the N atom linking them, form a piperidine, morpholine, hexamethylenimine (perhydroazepine), pyrrolidine, piperazine or 1-methylpiperazine radical, and R$^6$ and R$^7$ are alkyl having 1 to 18 C atoms or alkyl having 2 to 20 C atoms which are interrupted by one or more groups from the series comprising —O—, —S—, —NH—,

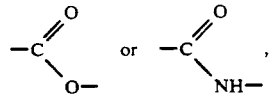

or an unsubstituted or C$_1$-C$_8$alkyl-substituted cycloalkyl group having 5 to 12 ring C atoms, an unsubstituted or C$_1$-C$_8$alkyl-substituted C$_5$-C$_{12}$cycloalkyl-C$_1$-C$_4$alkyl group, an unsubstituted or C$_1$-C$_8$alkyl-substituted C$_3$-C$_{12}$cycloalkyl-C$_1$-C$_4$alkyl group which is interrupted by one or more groups from the series comprising —O—, —S—, —NH—,

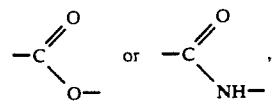

or phenyl, naphthyl, C$_7$-C$_{18}$alkaryl or C$_7$-C$_{18}$aralkyl.

2. A composition according to claim 1, containing a compound of the formula Ia, in which R$^1$ is alkyl having 1 to 18 C atoms, phenyl or benzyl and R$^2$ is —O—(C$_1$-C$_{18}$)alkyl, —N[(C$_1$-C$_{18}$)alkyl]$_2$, —O—(C$_5$-C$_{12}$)cycloalkyl, —O-phenyl, —O—(C$_7$-C$_{18}$)aralkyl, —S—(C$_1$-C$_{12}$)alkyl, —S-phenyl, —S—(C$_7$-C$_{18}$)aralkyl or —S—CH$_2$—COOR$^9$, R$^9$ being C$_1$-C$_{18}$alkyl.

3. A composition according to claim 1, containing a compound of the formula Ia, in which R$^1$ is alkyl having 9 to 18 C atoms or phenyl and R$^2$ is —O—(C$_1$-C$_{18}$)alkyl, —S—(C$_8$-C$_{10}$)alkyl, —N[(C$_4$-C$_8$)alkyl]$_2$, —S—CH$_2$—COO(C$_2$-C$_8$)alkyl or —S-benzyl.

4. A composition according to claim 1, containing a compound of the formula Ia, in which R$^1$ is phenyl and R$^2$ is —SR$^7$ or —S—CH$_2$COOR$^9$, and R$^7$ is C$_4$-C$_{12}$alkyl and R$^9$ is C$_4$-C$_{12}$alkyl.

5. A composition according to claim 1 wherein

R$^1$ is alkyl having 1 to 18 C atoms, cycloalkyl having 5 to 8 ring C atoms, phenyl or C$_7$-C$_{18}$aralkyl, R$^4$ and R$^5$ are identical or different and are —H, alkyl having 1 to 18 C atoms, cycloalkyl having 5 to 12 ring C atoms or phenyl, and R$^6$ and R$^7$ are alkyl having 1 to 18 C atoms, a cycloalkyl group having 5 to 8 ring C atoms or alkyl having 2 to 20 C atoms and interrupted by one group

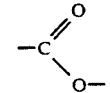

or phenyl or C$_7$-C$_{18}$aralkyl.

6. A composition comprising
(a) a lubricant or hydraulic fluid, and
(b) at least one compound of formula Ib

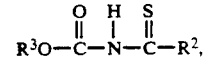
(Ib)

R$^3$ is alkyl having 1 to 25 C atoms, an unsubstituted or C$_1$-C$_8$alkyl-substituted cycloalkyl group having 5 to 12 ring C atoms, an unsubstituted or C$_1$-C$_8$alkyl-substituted C$_5$-C$_{12}$cycloalkyl-C$_1$-C$_4$alkyl group, alkenyl having 2 to 18 C atoms, phenyl, naphthyl, C$_7$-C$_{18}$aralkyl or C$_7$-C$_{18}$alkaryl, or R$^3$ is alkyl having 1 to 25 C atoms, an unsubstituted or C$_1$-C$_8$alkyl-substituted cycloalkyl group having 5 to 12 ring C atoms, an unsubstituted or C$_1$-C$_8$alkyl-substituted C$_5$-C$_{12}$cycloalkyl-C$_1$-C$_4$alkyl group, alkenyl having 2 to 18 C atoms, phenyl, naphthyl, C$_7$-C$_{18}$aralkyl or C$_7$-C$_{18}$alkaryl, each of which are monosubstituted or polysubstituted by group from the series comprising halogen, cyano, nitro, —OR$^a$ or —COOR$^b$, or R$^3$ is alkyl having 2 to 25 C atoms, an unsubstituted or C$_1$-C$_8$alkyl-substituted cycloalkyl group having 3 to 10 ring C atoms, an unsubstituted or C$_1$-C$_8$alkyl-substituted C$_3$-C$_{12}$cycloalkyl-C$_1$-C$_4$alkyl group, alkenyl having 3 to 18 C atoms, C$_7$-C$_{18}$aralkyl or C$_7$-C$_{18}$alkaryl, each of which are interrupted by one or more groups from the series comprising —O—, —S—, —NH—,

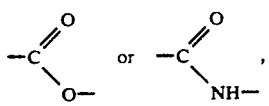

C$_7$-C$_{18}$aralkyl or C$_7$-C$_{18}$alkaryl being interrupted only in the alkyl radicals, or R$^3$ is alkyl having 2 to 25 C atoms, an unsubstituted or C$_1$-C$_8$alkyl-substituted cycloalkyl group having 3 to 10 ring C atoms, an unsubstituted or C$_1$-C$_8$alkyl-substituted C$_3$-C$_{12}$cycloalkyl-C$_1$-C$_4$alkyl group, alkenyl having 3 to 18 C atoms, C$_7$-C$_{18}$aralkyl or C$_7$-C$_{18}$alkaryl, each of which are monosubstituted or polysubstituted by groups from series comprising halogen, cyano, nitro, —OR$^a$ or —COOR$^b$ and are each interrupted by one or more groups from the series comprising —O—, —S—, —NH—,

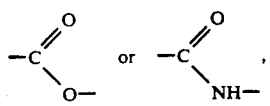

the C$_7$-C$_{18}$aralkyl or C$_7$-C$_{18}$alkaryl being interrupted only in the alkyl radicals,
R$^a$ being as defined for R$^3$ with the exception of —OR$^a$,
R$^b$ being as defined for R$^6$,
R$^2$ is —OR$^6$ or —SR$^7$, and
R$^6$ and R$^7$ are alkyl having 1 to 18 C atoms or alkyl having 2 to 20 C atoms which are interrupted by one or more groups from the series comprising —O—, —S—, —NH—,

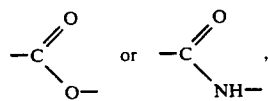

or an unsubstituted or C$_1$-C$_8$alkyl-substituted cycloalkyl group having 5 to 12 ring C atoms, an unsubstituted or C$_1$-C$_8$alkyl-substituted C$_5$-C$_{12}$cycloalkyl-C$_1$-C$_4$alkyl group, an unsubstituted or C$_1$-C$_8$alkyl-substituted C$_3$-C$_{12}$cycloalkyl-C$_1$-C$_4$alkyl group which is interrupted by one or more groups from the series comprising —O—, —S—, —NH—,

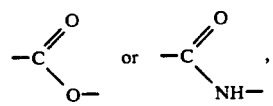

or phenyl, naphthyl, C$_7$-C$_{18}$alkaryl or C$_7$-C$_{18}$aralkyl.

7. A composition according to claim 6, containing a compound of the formula Ib, in which R$^2$ is —O—(C$_1$-C$_{18}$)alkyl, —O—(C$_5$-C$_{12}$)cycloalkyl, —O-phenyl, —O—(C$_7$-C$_{18}$)aralkyl, —S—(C$_1$-C$_{12}$)alkyl, —S-phenyl, —S—(C$_7$-C$_{18}$)aralkyl or —S—CH$_2$—COOR$^9$,
R$^9$ being C$_1$-C$_{18}$alkyl and
R$^3$ being C$_1$-C$_{18}$alkyl, cyclohexyl, phenyl or benzyl.

8. A composition according to claim 6, containing a compound of the formula Ib, in which R$^2$ is —O—(C$_2$-C$_8$)alkyl, —S—(C$_8$-C$_{12}$)alkyl and R$^3$ is C$_2$-C$_4$alkyl, cyclohexyl or phenyl.

9. A composition according to claim 6, containing a compound of the formula Ib, in which R$^2$ is —SR$^7$ or —S—CH$_2$—COOR$^9$, R$^7$ being C$_4$-C$_{12}$alkyl, R$^9$ being C$_4$-C$_{12}$alkyl and R$^3$ being C$_1$-C$_4$alkyl, cyclohexyl or phenyl.

10. A composition according to claim 6, containing a compound of the formula Ib, in which R$^2$ is -S-n-octyl and R$^3$ is ethyl, and/or a compound of the formula Ib, in which R$^2$ is —S—(2-ethylhexyl) and R$^3$ is n-butyl.

11. A composition according to claim 5 wherein
R$^3$ is alkyl having 1 to 18 C atoms, cycloalkyl having 5 to 8 ring C atoms, phenyl or C$_7$-C$_{18}$aralkyl, and
R$^6$ and R$^7$ are alkyl having 1 to 18 C atoms, a cycloalkyl group having 5 to 8 ring C atoms or alkyl having 2 to 20 C atoms and interrupted by one group

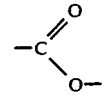

or phenyl or C$_7$-C$_{18}$aralkyl.

* * * * *